(12) United States Patent
Johnston et al.

(10) Patent No.: US 6,632,806 B1
(45) Date of Patent: Oct. 14, 2003

(54) NEUROLOGICALLY-ACTIVE COMPOUNDS

(75) Inventors: Graham A. R. Johnston, Roseville (AU); Peter M. Burden, Annandale (AU); Kenneth Noel Mewett, Newtown (AU); Mary Chebib, Darlington (AU)

(73) Assignees: The University of Sydney, Sydney (AU); Polychip Pharmaceuticals Pty. Ltd., Toorak (AU)

( * ) Notice: Subject to any disclaimer, the term of this patent is extended or adjusted under 35 U.S.C. 154(b) by 0 days.

(21) Appl. No.: 09/446,721

(22) PCT Filed: Jun. 23, 1998

(86) PCT No.: PCT/AU98/00485

§ 371 (c)(1),
(2), (4) Date: Dec. 22, 1999

(87) PCT Pub. No.: WO98/58939

PCT Pub. Date: Dec. 30, 1998

(30) Foreign Application Priority Data

| Jun. 23, 1997 | (AU) | ................................................ PO7501 |
| Apr. 17, 1998 | (AU) | ................................................ PP2985 |

(51) Int. Cl.$^7$ ........................................... A61K 31/675
(52) U.S. Cl. ............................................................ 514/89
(58) Field of Search ............................................ 514/89

(56) References Cited

U.S. PATENT DOCUMENTS

| 5,376,684 A | 12/1994 | Mickel ........................ 514/553 |
| 5,545,631 A | 8/1996 | Marescaux et al. ........... 514/89 |
| 5,627,169 A | * 5/1997 | Miledi et al. .................. 514/89 |

OTHER PUBLICATIONS

Remington's Pharmecutical Sciences, Gennaro et al Eds., Mack Publishing , Easton, PA, p. 1418.*
European Search Report for EPO Application Ser. No. EP 98 92 9133.1, mailed Jan. 17, 2001.
International Search Report for PCT Application Ser. No. PCT/AU98/000485, mailed Sep. 28, 1998.

* cited by examiner

*Primary Examiner*—Russell Travers
(74) *Attorney, Agent, or Firm*—Williams, Morgan and Amerson

(57) ABSTRACT

The invention provides methods for enhancing cognitive activity and stimulating memory capacity, comprising the step of administering an effective amount of a compound with $GABA_C$ receptor antagonist activity to an animal in need of such treatment. Preferably the compound has selective $GABA_C$ receptor antagonist activity, and more preferably comprises a phosphinic acid group. The invention also provides novel compounds and compositions. The methods of the invention are useful in the treatment of dementias and conditions involving cognitive deficit, or memory impairment.

16 Claims, 8 Drawing Sheets

A.

B.

NEUROLOGICALLY-ACTIVE COMPOUNDS

The present application is a nationalization of International Patent Application PCT/AU98/00485, filed Jun. 23, 1998, which claims priority to Australian Patent Application PP 7501, filed Jun. 23, 1998, 1997.

This invention relates to neurologically-active compounds, and to methods of use thereof. In particular the invention relates co methods of enhancing cognitive activity using compounds which are antagonists of $GABA_C$ receptors. Preferred compounds for use in the methods of the invention are TPMPA and analogues thereof, and novel compounds are disclosed.

BACKGROUND OF THE INVENTION

There are three major classes of GABA receptors in the central nervous system (CNS): $GABA_A$, $GABA_B$ and $GABA_C$ receptors. The pharmacology of $GABA_A$ and $GABA_B$ receptors has been extensively investigated, but $GABA_C$ receptors have been only recognised recently, and their pharmacological potential is still unknown (Johnston, 1996b).

γ-Aminobutyric acid (GABA) is the main inhibitory neurotransmitter in the central nervous system (CNS), and activates three major subtypes of GABA receptors, the $GABA_A$, $GABA_B$ and $GABA_C$ receptors. $GABA_A$ receptors are ligand-gated Cl$^-$ channels which are inhibited by the alkaloid bicuculline (Johnston, 1996a). These are heterooligomeric receptors made up of α, β, γ, and δ subunits. $GABA_B$ receptors are transmembrane receptors coupled to second messenger systems and $Ca^{2+}$ and $K^+$ channels via G-proteins. These receptors are not blocked by bicuculline, but are activated by (−)baclofen and 3-aminopropylphosphinic acid (CGP27492) and blocked by phaclofen and saclofen (Kerr and Ong, 1995).

$GABA_C$ receptors (sometimes called $GABA_{NANB}$ or r receptors) were first proposed when a series of conformationally restricted GABA analogues, including cis-4-aminocrotonic acid (CACA), that had bicuculline-insensitive depression actions on neuronal activity, showed no affinity for [$^3$H]baclofen binding sites in rat cerebellar membranes (Drew et al, 1984). $GABA_C$ receptors with similar pharmacology were first found in neurons from rat retina (Feigenspan et al, 1993) and white perch retina (Qian et al, 1993). In rat retina, rod bipolar cells contain bicuculline-insensitive, baclofen-insensitive receptors that were activated by CACA (Feigenspan et al, 1993). These were detected by the co-application of GABA with 100 μM bicuculline to abolish the $GABA_A$ component (Feigenspan et al, 1993). In white perch retina, rod-driven horizontal cells (H4) and not bipolar cells showed $GABA_C$ receptor-like pharmacology. Application of GABA on bipolar cells showed rapid desensitisation, while on rod-driven horizontal cells, desensitisation was not observed (Qian et al, 1993). Subsequently, $GABA_C$ receptors were found on cone-driven horizontal cells in catfish (Dong et al, 1994) and bipolar terminals in tiger salamander (Lukasiewicz et al, 1994).

The expression of mRNA from bovine retina in *Xenopus* oocytes showed that GABA activated two distinct GABA receptors Both receptors activated Cl$^-$ currents. One was mediated by $GABA_A$ receptors and was blocked by bicuculline, and the other was mediated by $GABA_C$ receptors and was insensitive to both bicuculline and baclofen (Polenzani et al, 1991). Subsequently, two cDNAs that have 30–38% sequence identity with $GABA_A$ receptor subunits were cloned from human retinal mRNA (Cutting et al, 1991; 1992). These subunits have been termed $r_1$ and $r_2$, and have 74% sequence identity (Cutting et al, 1991; 1992)

At least two major subtypes of $GABA_C$ receptors are now known, namely rho-1 and rho-2. As is known for other neurotransmitter receptor subtypes, different subtypes of $GABA_C$ receptors are likely so be involved in different aspects or nervous system function. As the rho-2 subunit is found in the hippocampus and neocortex, and these areas of the brain are important for memory, potent and selective agents for the rho-2 $GABA_C$ receptor are key compounds.

The species equivalents of the human $r_1$ and $r_2$ subunits have been cloned from rat (Enz et al, 1995). These show 88–99% homology with the respective human sequences. The use of PCR and in situ hybridisation have shown high expression of both the $r_1$ and $r_2$ subunits in rod bipolar cells. However, only the $r_2$ subunit is expressed in the CNS, particularly in the hippocampus and cortex (Enz et al, 1995). Recently, a third r subunit was cloned from rat retina cDNA (Ogurusu and Shingai, 1996). This subunit exhibits 63% and 61% sequence homology to the human $r_1$ and rat $r_2$ sequences respectively (Ogurusu and Shingai, 1996).

Expression of human r subunits in *Xenopus* oocytes generates homooligomeric GABA receptors with intrinsic Cl$^-$ channels. These receptor ion channels are activated by GABA and CACA, but are insensitive to bicuculline, (−)baclofen, barbiturates and benzodiazepines. They have been shown to be sensitive to picrotoxin, and have been classified as $GABA_C$ receptors (Cutting et al, 1991; 1992; Polenzani et al, 1991; Shimada et al, 1992; Kusama et al, 1993a; 1993b; Wang et al, 1994; Bormann and Feigenspan, 1995; Johnston, 1996b).

The most potent $GABA_C$ receptor agonists known so far are trans-4-aminocrotonic acid (TACA, $K_D$=0.6 μM) and GABA ($K_D$=1.7 μM) (Woodward et al, 1993). TACA, a conformationally restricted analogue of GABA in an extended conformation, is also a $GABA_A$ receptor agonist (Johnston, 1996a). CACA, a conformationally-restricted analogue of GABA in a folded conformation, has moderate partial agonist activity at $GABA_C$ receptors ($K_D$=74 μM), and may be the most selective agonist for this receptor subtype (Johnston, 1996b).

Selective agonists and antagonists are needed to determine the physiological role of $GABA_C$ receptors and to provide more specific therapeutic agents with a lower risk of unwanted side-effects. GABA is a flexible compound, due to its rotation about the C2–C3 and C3–C4 bonds. It can exist in a range of low energy conformations (Johnston et al, 1978; Allan and Johnston, 1983). Two of these conformations have been restricted by the introduction of unsaturation in the form of a double bond at the C2–C3 position, and two compounds that represent these restricted conformations are CACA and TACA (Johnston et al, 1975). CACA and TACA have fewer degrees of rotational freedom than GABA, and can only rotate about the C3–C4 bond (Johnston et al, 1978; Allan and Johnston, 1983). CACA is a partially folded analogue of GABA. It has moderate activity at $GABA_C$ receptors expressed in *Xenopus* oocytes, and although its agonist activity is weak, it is to date the most selective agonist at these receptors, having minimal activity on $GABA_A$ and $GABA_B$ receptors (Johnston, 1996b). TACA is an extended analogue of GABA. It has potent agonist activity at $GABA_C$ receptors expressed in *Xenopus* oocytes; however, it is not selective, as it is also a potent $GABA_A$ receptor agonist (Johnston, 1996b).

Woodward et al (1993), using poly(A)$^+$ RNA from mammalian retina expressed in *Xenopus* oocytes; tested many GABA$_A$ and GABA$_B$ receptor agonists and antagonists to determine a pharmacological profile for GABA$_C$ receptors. From this study, it was found that the phosphinic and methylphosphinic analogues of GABA, which are known to be potent GABA$_B$ receptor agonists, were potent antagonists at GABA$_C$ receptors.

A series of GABA analogues was tested for agonist and antagonist activity at GABA$_C$ receptors, using poly(A)$^+$. RNA from mammalian retina injected into *Xenopus oocytes*. Several potent GABA$_C$ receptor antagonists were identified, including (3-aminopropyl)methylphosphinic acid (CGP35024; K$_B$=0.8 μM), 3-aminopropylphosphinic acid (CGP27492; K$_B$=1.8 μM), and 3-aminopropylphosphonic acid (3-APA, K$_B$=10 μM) (Woodward et al, 1993). These agents are not selective for GABA$_C$ receptors, as CGP35024 and CGP27492 are also very potent GABA$_B$ receptor agonists, while 3-APA is a GABA$_B$ receptor antagonist.

To date, only one specific GABA$_C$ receptor antagonist has been described. A more recently synthesised compound, 1,2,5,6-tetrahydropyridine-4-yl)methylphosphinic acid (TPMPA), does show potent and selective GABA$_C$ receptor antagonist activity (K$_D$=2.1 μM) (Murata et al, 1996; Ragozzino et al, 1996). TPMPA produces 50% inhibition or GABA$_C$ receptor activation at 2.1 μM, and has the following structure:

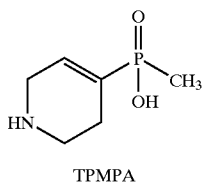

TPMPA

The effects of TPMPA on cognition are unknown.

As a result of the structure-activity relationship study and the selectivity of CACA for GABA$_C$ receptors, we have investigated the methylphosphinic acid and phosphinic acid analogues of CACA and the closely related analogue, TACA, as potential GABA$_C$ receptor antagonists. In this study, we demonstrate that the phosphinic and methylphosphinic acid derivatives of CACA and TACA, and 3-aminopropyl-n-butyl-phosphinic acid (CGP36742), an orally-active GABA$_B$ receptor antagonist, are GABA$_C$ receptor antagonists, and we have linked GABA$_C$ receptors with cognitive function. Extensive structure-activity studies were carried out on recombinant GABA$_C$ receptors from human retina expressed in frog oocytes. Among the compounds studied were a variety of compounds known to interact with GABA$_B$ receptors, provided by Ciba-Geigy AG, Basle.

The most interesting of the Ciba-Geigy compounds were a series of GABA$_B$ receptor antagonists that had been investigated in various memory and learning tests in rats and mice only one compound of the series reversed age-related deficits of old rats (Froestl, 1995b). The cognition-enhancing effects of this compound were confirmed in learning experiments in monkeys. This compound had good oral bioavailability in rats and dogs, and in healthy young and elderly male volunteers. On this basis it was selected as a development compound for the treatment of cognition deficits.

The cognition-enhancing compound, (3-aminopropyl)-n-butylphosphinic acid, code-named CGP36742, has she following structure:

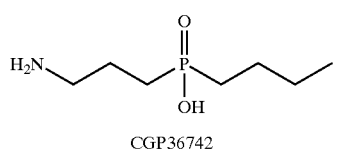

CGP36742

The GABA$_B$ antagonist properties of CGP36742 do not satisfactorily explain its cognition-enhancing properties, since much more potent GABA$_B$ antagonists have been described that lack these properties.

We have now surprisingly found that CGP36742 has similar potency as a GABA$_C$ antagonist to its potency as a GABA$_B$ antagonist (50% inhibition of receptor activation being found at 38 μM and 62 μM against GABA$_B$ and GABA$_C$ receptors respectively). None of the other potent GABA$_B$ antagonists showed activity against GABA$_C$ receptors. These findings indicate a likely role for GABA$_C$ receptor antagonism in the cognition-enhancing properties of CGP36742.

SUMMARY OF THE INVENTION

In one aspect the invention provides a method of enhancing the cognitive activity of an animal in need of such treatment, comprising the step of administering an effective amount of a compound which has GABA$_C$ receptor antagonist activity to said animal.

In a second aspect the invention provides a method of stimulating memory capacity, comprising the step of administering an effective amount of a compound which has GABA$_C$ receptor antagonist activity to an animal in need of such treatment.

The methods of the invention are suitable for the treatment of a variety of cognitive deficit conditions, dementias, and memory impairment conditions, including but not limited to those associated with Alzheimer's disease, AIDS, and schizophrenia.

Preferably the compound has selective antagonist activity against GABA$_C$ receptors compared with GABA$_B$ receptors. More preferably, the compound has selective antagonist activity against GABA$_C$ receptors compared with GABA$_A$ receptors. Even more preferably, the compound is substantially inactive against both GABA$_A$ and GABA$_B$ receptors.

More preferably the compound comprises a phosphinic acid group, and even more preferably comprises an alkyl-substituted phosphinic acid group in which the alkyl group is of 1 to 6 carbon atoms, such as a methyl or ethyl phosphinic acid group. Most preferably the compound also comprises a double bond which imposes a conformational restriction on rotation about the bond corresponding to the C3–C4 bond of GABA. Particularly preferred compounds include, but are not limited to, conformationally-restricted analogues of CGP44530 in which rotation about the C3–C4 bond is restricted, such as TPMPA and analogues thereof.

Thus preferred compounds of the invention are represented by general formula I or general formula II,

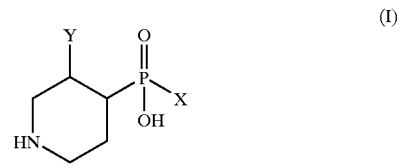

(I)

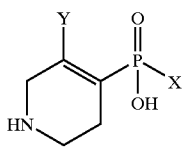

(II)

in which X represents hydrogen, an alkyl group optionally substituted with a halogen, or a hydroxyalkyl group, and Y represents hydrogen, a halogen, or an alkyl, alkenyl, alkynyl or acyl group, optionally substituted wish halogen, nitrile, or $NO_2$.

In general formula I, Y may also be an alkoxy group, optionally substituted with halogen, nitrile or $NO_2$.

By "alkyl" is meant a straight or branched, saturated or unsaturated, substituted or unsubstituted alkyl chain of 1 to 6, preferably 1 to 4 carbon atoms, and includes alicyclic alkyl chains such as cyclopropylethyl. Alkenyl, alkynyl and acyl also refer to groups of 1–6, preferably 1–4 carbon atoms. The halogen is preferably chlorine or fluorine.

It will be clearly understood that some of the compounds which are useful for the purposes of the invention are novel, and form part of the invention. Thus in a third aspect the invention provides a compound having $GABA_C$ antagonist activity and selectivity for the rho-2 subtype of $GABA_C$ receptors of general formula II as defined above. Thus in a third aspect the invention provides a compound having $GABA_C$ antagonist activity and selectivity for the rho-2 subtype of $GABA_C$ receptors of general formula II as defined above.

In a fourth aspect, the invention provides a composition comprising a compound of general formula II, together with a pharmaceutically-acceptable carrier.

While the invention is not in any way restricted to treatment of any particular animal species, in general the animal will be a human.

The compounds may be administered at any suitable dose and by any suitable route. Oral administration is preferred because of its greater convenience and acceptability. The effective dose will depend on the nature of the condition to be treated, and the age, weight and underlying state of health of the individual to be treated, and will be at the discretion of the attending physician or veterinarian. Suitable dosage levels may readily be determined by trial and error experimentation, using methods which are well known in the art. Similarly, suitable formulations for administration by any desired route may be prepared by standard methods, for example by reference to well-known texts such Remington: The Science and Practice of Pharmacy, Volume II, 1995 (19$^{th}$ edition), A. R. Gennaro (Ed), Mack Publishing Company, Easton, Pa. 18042, USA., or Australian Prescription Products Guide, Volume 1, 1995 (24$^{th}$ edition), J Thomas (Ed), Australian Pharmaceutical Publishing Company Limited, Victoria, Australia.

Throughout the description and claims of this specification, the word "comprise" and variations of the word, such as "comprising" and "comprises", means "including but not limited to" and is not intended to exclude other additives, components, integers or steps.

DETAILED DESCRIPTION OF THE INVENTION

Figure 1:
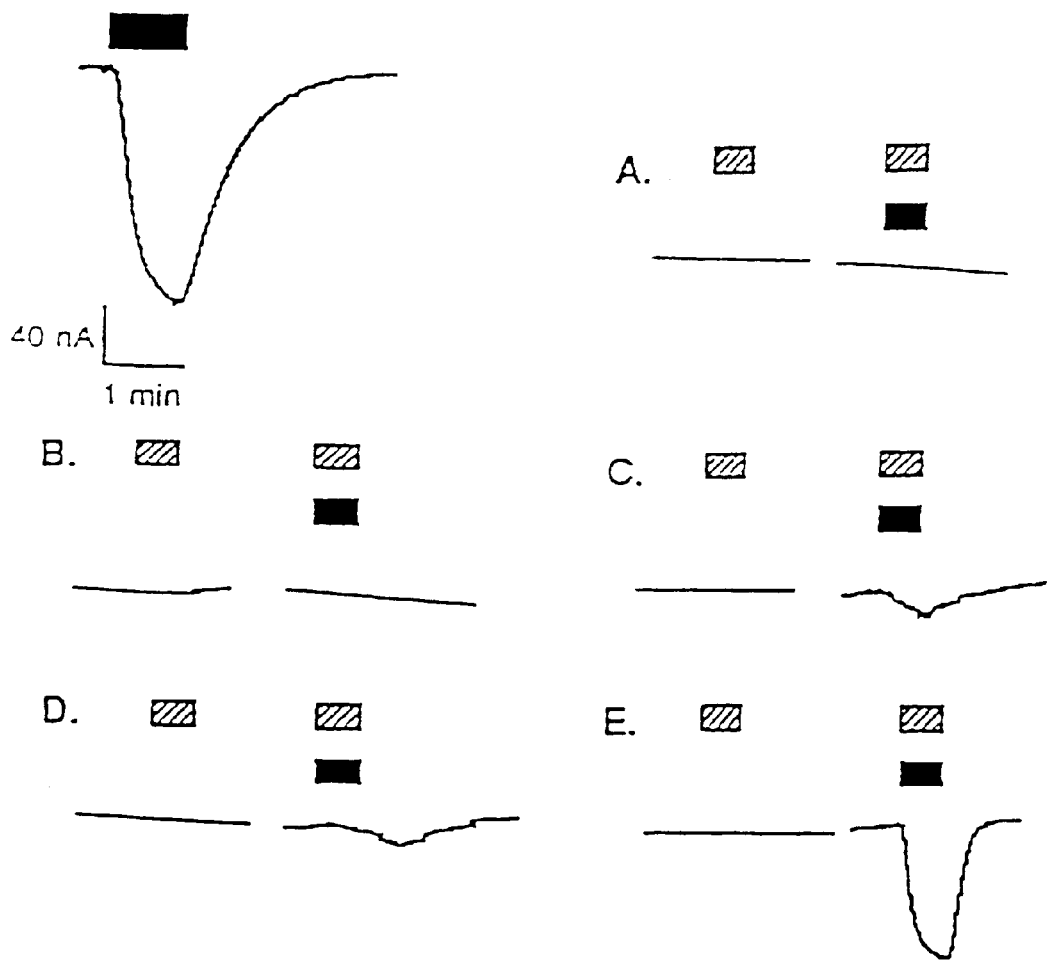
FIG. 1 shows that expression of human $r_1$ receptors in Xenopus oocytes produces homooligomeric GABA receptors ($GABA_C$ receptors) with intrinsic Cl$^-$ channels. GABA (1 $\mu$M) activates the Cl$^-$ channels (duration indicated by filled bar) and produces an inward current when the oocyte is clamped at $-60$ mV. (A) CGP38593 (100 $\mu$l), (B) CGP44530 (100 $\mu$M), (C) CGP70523 (100 $\mu$M), (D) CGP36742 (100 $\mu$M), and (E) CGP70522 (300 $\mu$M) do not activate the receptor (duration indicated by hatched bar). However, when (A) CGP38593 (100 $\mu$M), (B) CGP44530 (100 $\mu$M), (C) CGP70523 (100 $\mu$M), (D) CGP36742 (100 $\mu$M), and (E) CGP70522 (300 $\mu$M) are co-applied with GABA (1 $\mu$M), the GABA response is blocked or reduced.

The invention is described in detail by way of reference only to the following non-limiting general methods and experimental examples, and to the figures.

Materials

[(E)-3-Aminopropen-1-yl]methylphosphinic acid (CGP44530),

[(E)-3-aminopropen-1-yl]phosphinic acid (CGP38593),

[(Z)-3-aminopropen-1-yl]methylphosphinic acid (CGP70523),

[(Z)-3-aminopropen-1-yl]phosphinic acid (CGP70522), 3-aminopropyl-n-butyl-phosphinic acid (CGP36742), 3-aminopropyl(diethoxymethyl)phosphinic acid (CGP35348), 3-aminopropyl(cyclohexylmethyl)phosphinic acid (CGP46381), (2S)-3-amino-2-hydroxypropyl(cyclohexylmethyl) phosphinic acid (CGP51176) and (2R, 1'S)-(3-N-[1'(3,4-dichlorophenyl)ethyl])amino-2-hydroxypropyl)benzylphosphinic acid (CGP55845A) were synthesised as described Previously by Froestl et al, (1992; 1995a; 1995b). CACA and TACA were prepared as previously described (Johnston et al, 1975). GABA was purchased from Sigma Chemical Co (St Louis, Mo., USA).

Electrophysiological Recording

Human $r_1$ cDNA in pcDNA (Invitrogen, San Diego, Calif., USA) was obtained from Dr. George Uhl (National Institute for Drug Abuse, Baltimore, USA). The plasmid was linearized with XbaI and cRNA made using the "Message Machine" kit from Ambion Inc. (Austin, Tex., USA). 50 ng of cRNA was injected into defolliculated Stage V Xenopus oocytes. Two to seven days later, receptor activity was measured by two-electrode voltage clamp recording, using a Geneclamp 500 amplifier (Axon Instruments Inc., Foster City, Calif., USA) and a MacLab 2e recorder (ADInstruments, Sydney, NSW, Australia). Oocytes were voltage clamped at −60 mV and continuously superfused with ND96 buffer (96 mM NaCl, 2 mM KCl, 1.8 mM $CaCl_2$, 1 mM $MgCl_2$ and 5 mM HEPES, pH 7.5). For receptor activation measurements, the indicated concentrations of agonist and antagonist were added to ND96.

Analysis of Kinetic Data

Current (I) as a function of agonist concentration ([A]) was fitted by least squares to $I=I_{max}[A]^{nH}/(EC_{50}{}^{nH}+[A]^{nH})$, where $I_{max}$ is the maximal current, the $EC_{50}$ is the effective dose that activates 50% of the maximal current and $n_H$ is the hill coefficient. $EC_{50}$ values are expressed as mean±S.E.M. (n=3–6) and were determined by fitting data from individual oocytes using Kaleidagraph 2.1 (1990). Current (I) as a function of antagonist concentration ([Ant]) was fitted by least squares to $I=I_{max}-\{I_{max}[Ant]^{nH}/(IC_{50}{}^{nH}+[Ant]^{nH})\}$, where the $IC_{50}$ is the inhibition dose that blocks 50% of the current generated by 1 µM GABA and $n_H$ is the hill coefficient. $IC_{50}$ values are expressed as mean±S.E.M. (n=3–6). $K_B$ values are the apparent dissociation constants for the antagonists, and were determined using Schild plot analysis (Arunlakshana and Schild, 1959). -log$K_B$ values were determined using the following equation: $\log\{(A)/(A^*)-1\}=m.\log[Ant]-\log K_B$, where A is the $EC_{50}$ of GABA in the presence of a known antagonist concentration, A* is the $EC_{50}$ of GABA in the absence of an antagonist, [Ant] is the concentration of the antagonist, and 'm' is the slope of the curve. For simple competitive antagonism, 'm' is 1. -log$K_B$ values were determined by fitting data to the above function using Kaleidagraph 2.1 (1990). Schild analyses were carried out for compounds that had $IC_{50}$ values of less than 30 µM.

EXAMPLE 1

GABA$_C$ Receptor Antagonists Block Activation of Chloride Channels by GABA

Figure 2:
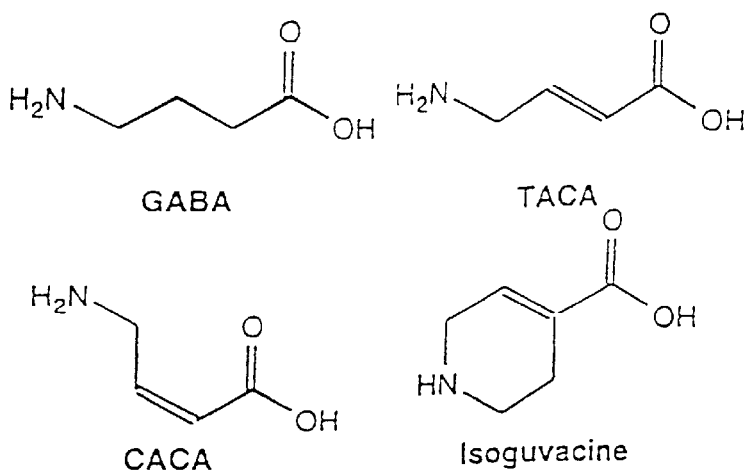
FIG. 2 shows (A) Structures of compounds that show agonist activity at $GABA_C$ receptors. (B) Structures of compounds that show antagonist activity at $GABA_C$ receptors.
Figure 2:
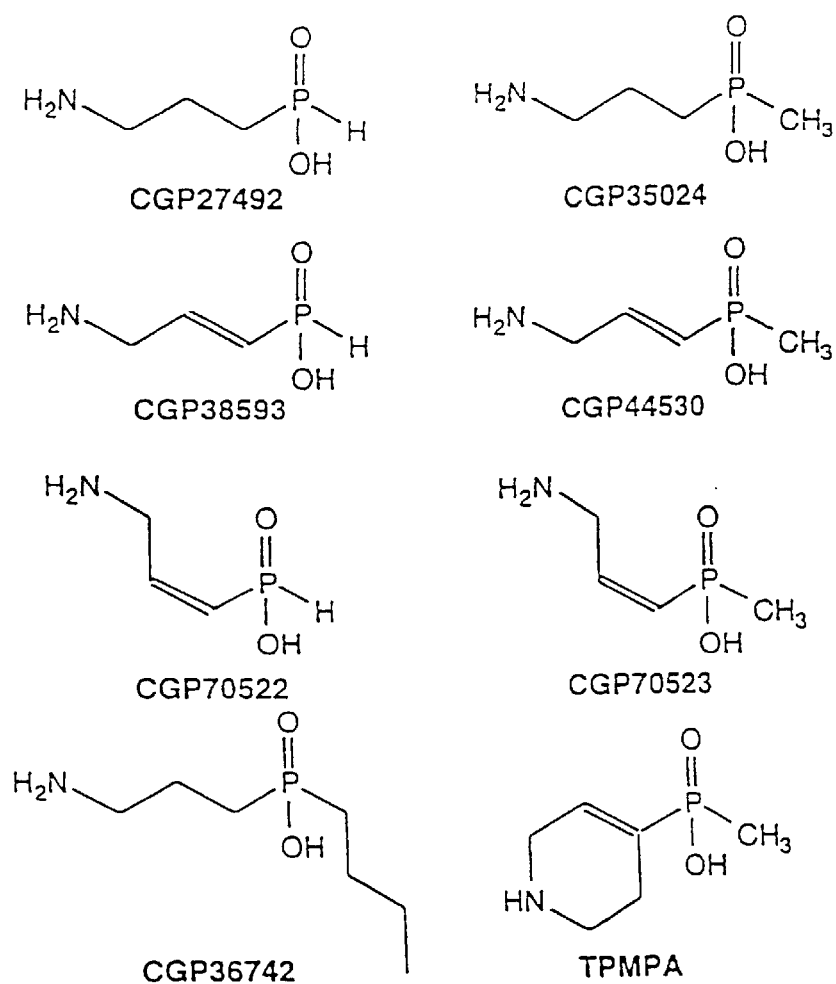
Figure 3:
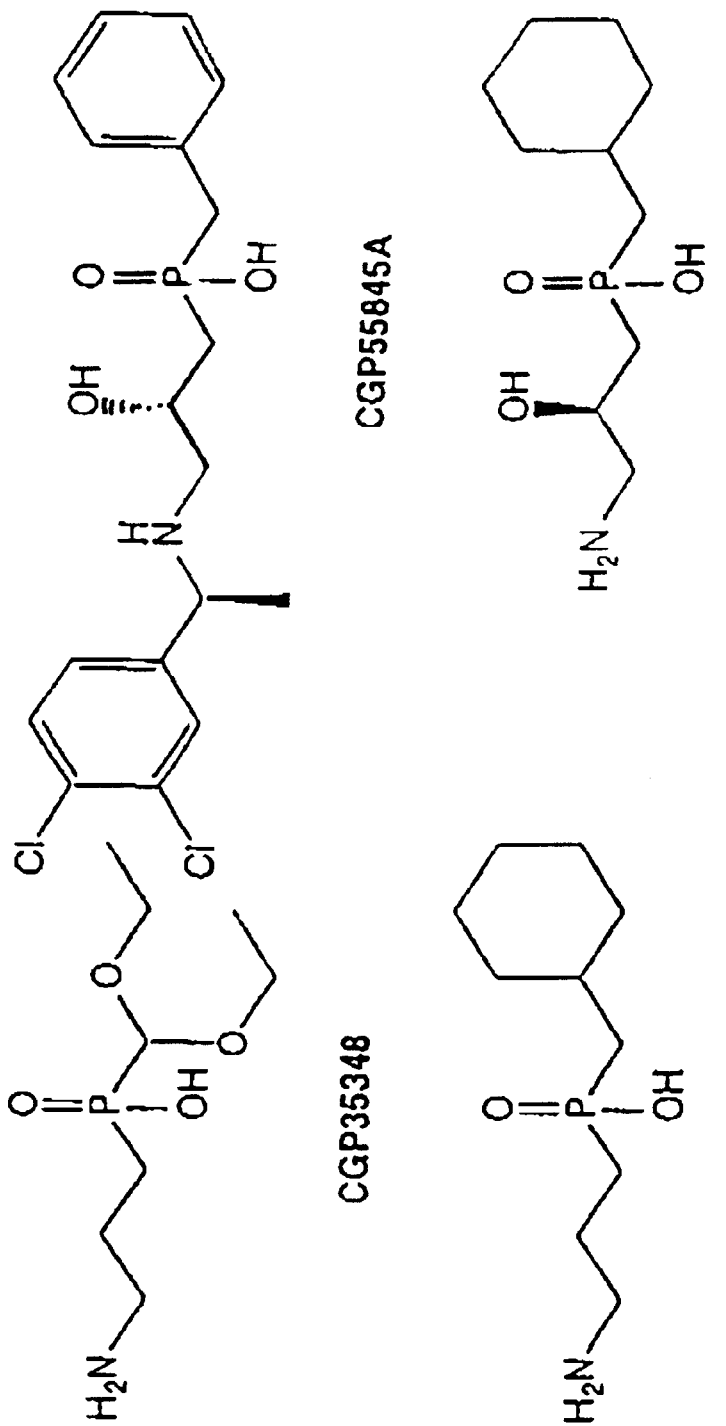
FIG. 3 shows structures of orally active $GABA_B$ receptor antagonists with no cognitive enhancement effects. These compounds show no affinity for $GABA_C$ receptors as either agonists or antagonists when tested at 100 $\mu$M.
Figure 4:
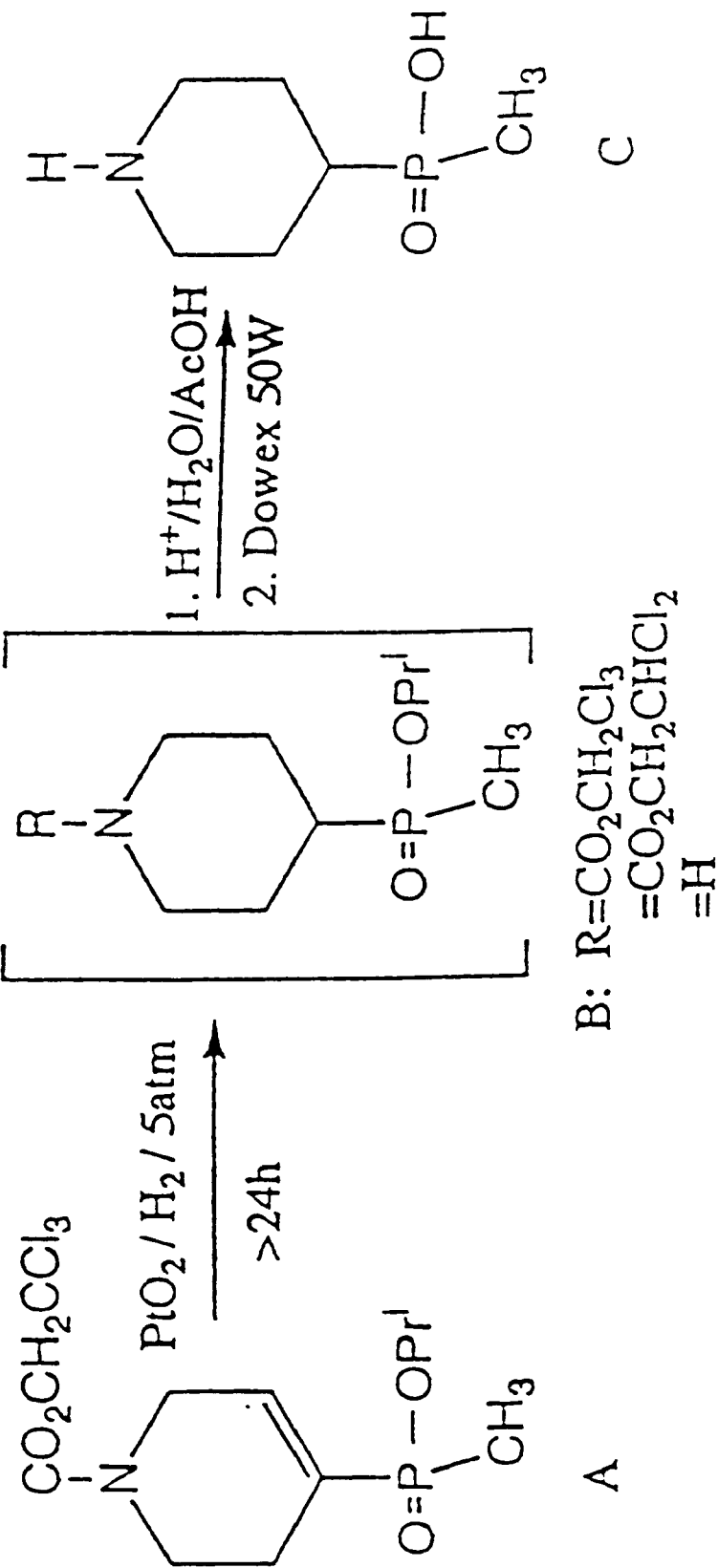
FIG. 4 summarizes the synthesis of PMPA by reduction of a precursor of TMPA and subsequent hydrolysis.

Expression of human $r_1$ mRNA in *Xenopus oocytes* generated GABA$_C$ receptors which showed a dose-dependent GABA activated inward current when the cell was voltage clamped at −60 mV. This could be blocked by compounds such as CGP44530, CGP38593, CGP70523, CGP70522 and CGP36742, as shown in FIG. 1. The structures of the compounds are shown in FIG. 2 and FIG. 3. These compounds were first screened at 100 µM to determine agonist activity, by activation of Cl⁻ channels, or antagonist activity, by blocking the activation of the channels by 1 µM GABA. FIG. 2 shows the active compounds that had some effect at 100 µM as agonists (FIG. 2A) or antagonists (FIG. 2B) at GABA$_C$ receptors, and FIG. 3 shows the compounds that had no effect at 100 µM as agonists or antagonists at GABA$_C$ receptors.

Only the carboxylic acids, TACA, GABA and CACA activated the Cl⁻ channel. TACA was more potent than GABA, with an $EC_{50}$ of 0.44±0.02 µM, and was almost a full agonist, with a maximal TACA dose generating 95% of the maximal GABA activated current. GABA was found to have an $EC_{50}$ value of 0.82±0.09 µM. CACA was less potent than GABA, with an $EC_{50}$ value of 37.4±6.1 µM, and was a partial agonist, with a maximal CACA dose generating 75% of the maximal GABA activated current. These results are summarised in Table 1. The Hill Coefficients ($n_H$) as shown in Tables 1 and 2 were greater or equal to 2, which suggests that more than one molecule of the agonist is required to bind before the Cl⁻ channels can open. These findings are in agreement with those of Woodward et al (1993).

TABLE 1

Summary of $EC_{50}$, $IC_{50}$, $K_B$ and Hill Coefficients of various agonists and antagonists at the GABA$_C$ Receptor Expressed in *Xenopus oocytes*.

|  | $EC_{50}$ (µM)[a] | $IC_{50}$ (µM)[b] | $n_H$[c] | $K_B$ (µM)[d] |
|---|---|---|---|---|
| GABA | 0.82 ± 0.09 |  | 2.6 ± 0.2 |  |
| TACA | 0.44 ± 0.02 |  | 2.4 ± 0.2 |  |
| CACA | 37.4 ± 6.1 |  | 2.2 ± 0.3 |  |
| Isoguvacine[e] | 99 |  |  |  |
| CGP35024 |  | 0.75 ± 0.07 | 1.8 ± 0.1 | 0.58 ± 0.14 |
| CGP44530 |  | 5.5 ± 1.2 | 2.4 ± 0.5 | 8.6 ± 1.6 |
| CGP70523 |  | 38.9 ± 4.9 | 1.6 ± 0.1 |  |
| CGP27492 |  | 2.47 ± 0.04 | 1.9 ± 0.2 | 3.2 ± 1.0 |
| CGP38593 |  | 7.7 ± 0.7 | 1.8 ± 0.4 | 15.5 ± 1.7 |
| CGP70522 |  | >100 |  |  |
| CGP36742 |  | 62.5 ± 0.5 | 3.0 ± 0.4 |  |
| TPMPA[e] |  |  |  | 2.1 |

[a]$EC_{50}$ is the effective dose that activates 50% of the maximal current when tested at $r_1$ receptors expressed in *Xenopus oocytes*.
[b]$IC_{50}$ is the concentration that inhibits 50% of the response produced by 1 µM GABA. Data are the mean ± S.E.M. (n = 3–16 oocytes).
[c]$n_H$ is the Hill Coefficient.
[d]$K_B$ is the binding constant for the antagonist. These were determined using Schild plot analysis assuming competitive antagonism over the tested concentrations (Table 2).
[e]Data from Murata et al, 1996.

TABLE 2

Results of Schild Analyses of CGP35024, CGP27492, CGP44530 and CGP38593 at the GABA$_C$ Receptor Expressed in *Xenopus oocytes*.

| Antagonist | [Antagonist] (µM) | $EC_{50}$ (µM) of GABA[a] | $n_H$[b] | Slope of Schild Plot[c] |
|---|---|---|---|---|
| CGP35024 | 3 | 4.5 ± 0.1 | 2.3 ± 0.1 | 1.14 |
|  | 10 | 10.0 ± 1.4 | 2.2 ± 0.2 |  |
|  | 30 | 28.8 ± 4.2 | 1.9 ± 0.2 |  |
| CGP27492 | 10 | 3.2 ± 0.2 | 2.3 ± 0.1 | 0.99 |
|  | 30 | 9.3 ± 1.4 | 2.4 ± 0.3 |  |
|  | 100 | 25.7 ± 0.1 | 2.5 ± 0.2 |  |
| CGP44530 | 10 | 1.85 ± 0.04 | 2.6 ± 0.2 | 1.01 |
|  | 30 | 3.2 ± 0.2 | 3.0 ± 0.1 |  |
|  | 100 | 10.7 ± 0.5 | 3.7 ± 0.4 |  |
| CGP38593 | 30 | 2.5 ± 0.1 | 2.7 ± 0.1 | 0.95 |
|  | 60 | 4.1 ± 0.2 | 2.5 ± 0.4 |  |
|  | 100 | 6.8 ± 0.3 | 3.0 ± 0.1 |  |

[a] $EC_{50}$ is the effective dose that activates 50% of the maximal current when tested at $r_1$ receptors expressed in *Xenopus oocytes*. $EC_{50}$ values are expressed as mean±S.E.M. (n=3–6) and are determined by fitting data from individual oocytes using Kaleidagraph 2.1 (1990). $EC_{50}$ values of GABA have shifted to the right in the presence of a known concentration of the antagonist. -log $K_B$ values were determined as described in Materials and Methods section. The $K_B$ values are shown in Table 1.
[b] $n_H$ is the Hill Coefficient. These are greater than 1 indicating that more than 1 molecule of GABA is required for the channel to open.
[c] Slope of Schild plot analysis indicating competitive antagonism over the tested concentrations.

GP35024, CGP27492, CGP44530, CGP38593, CGP70523 and CGP70522 did not activate any current on their own (FIG. 1). They acted as $GABA_C$ receptor antagonists, inhibiting the current activated by 1 μM GABA (FIG. 1). $IC_{50}$ values were obtained for these compounds (Table 1) and Schild analyses were carried out for the active compounds (Table 2). $K_B$ (binding constant) values for CGP27492, CGP44530, CGP35024, and CGP38593 are shown in Table 1.

The methylphosphinic analogue, CGP44530, and phosphinic analogue, CGP38593 of TACA were antagonists with $IC_{50}$ values of 5.5±1.2 μM and 7.7±0.7 μM respectively. These compounds had lower affinity for the $GABA_C$ receptor expressed in *Xenopus oocytes* than that of the corresponding methylphosphinic analogue, CGP35024, and phosphinic analogue, CGP27492, of GABA. CGP35024 had an $IC_{50}$ of 0.75±0.07 μM and CGP27492 had an $IC_{50}$ of 2.47±0.04 μM. The methylphosphinic analogue, CGP70523 and phosphinic analogue, CGP70522, of CACA were antagonists, with $IC_{50}$ values of 38.9±4.9 μM and >100 μM respectively. These compounds had lower affinity for $GABA_C$ receptors than the methylphosphinic and phosphinic analogues of GABA and TACA. The order of potency of the methyl phosphinic acids and phosphinic acids is CGP35024>CGP27492>CGP44530>CGP38593>CGP70523>>CGP70522.

The new compounds CGP44530, CGP38593, CGP70523 and CGP70522 were weaker at the $GABA_C$ receptor than the existing phosphinic acid, CGP27492 and the methylphosphinic acid, CGP35024.

CGP35024, CGP27492, CGP44530 and CGP38593 were found to be competitive antagonists. The gradients of the Schild regression plots were not significantly different from 1 over the concentrations tested, indicating that these compounds compete for the same site as GABA.

CGP36742 was found to be an antagonist with moderate potency at the $GABA_C$ receptor, with an $IC_{50}$ value of 62.5±0.5 μM. This compound is orally active, showing cognitive enhancement effects. Other related compounds, such as CGP35348, CGP46381, CGP51176 and CGP55845A (FIG. 3), are also orally active, but do not show cognitive enhancement effects. These were screened at 100 μM, and had no effect as either agonists or antagonists at $GABA_C$ receptors. These compounds show high selectivity as $GABA_B$ receptor antagonists.

EXAMPLE 2

Relative Effects of Compounds on $GABA_A$, $GABA_B$ and $GABA_C$ Receptors

The development of many alkylphosphinic and phosphinic analogues of GABA has yielded novel $GABA_B$ receptor agonists and antagonists (Olpe et al, 1990; 1993; Bittiger et al, 1992; 1993; Froestl et al, 1992; 1995a; 1995b), including the methylphosphinic and phosphinic analogues of TACA and CACA, ie. CGP44530, CGP38593, CGP70522 and CGP70523. In this study, we tested these compounds on $GABA_C$ receptors expressed in *Xenopus oocytes*, and found them to be competitive antagonists. The antagonist potencies of CGP44530, CGP38593, CGP70522 and CGP70523 were found to be lower than that of the methylphosphinic and phosphinic analogues of GABA, CGP35024 and CGP27492.

The relative effects of the compounds at $GABA_A$, $GABA_B$ and $GABA_C$ receptors are shown in Table 3. Three compounds, CGP38593, CG?70522 and CGP27492, were moderately potent at $GABA_A$ receptors when tested using radioligand binding assays ($IC_{50}$=6.8 μM; $IC_{50}$=6.6 μM and $IC_{50}$=1.7 μM, respectively) (Froestl et al, 1995a). However, the compounds were more potent at $GABA_B$ receptors than at $GABA_A$ receptors using this assay. Similarly, these compounds appear more potent at $GABA_B$ receptors than at $GABA_C$ receptors.

TABLE 3

Affinities of the compounds used in this study at GABA receptors.

| Compound | Receptor Affinity[a] | | |
|---|---|---|---|
| | $GABA_A$ (μM)[b] | $GABA_B$ (μM)[c] | $GABA_C$ (μM)[d] |
| GABA | 0.128[k] | 0.033 | $EC_{50}$ = 0.82[e] |
| CGP27492 | 1.7[k] | 0.005 | 2.47 |
| CGP35024 | inactive at 10[k] | 0.016 | 0.75 |
| CGP36742 | 508 | 38 | 62 |
| TACA | 0.14[f,k] | inactive at 100[g] | $EC_{50}$ = 0.44[e] |
| CGP38593 | 6.8 | 0.28 | 7.68 |
| CGP44530 | inactive at 100 | 0.65 | 5.53 |
| CACA | 25[f,k] | inactive at 100[g] | $EC_{50}$ = 37[e] |
| CGP70522 | 6.6 | 4.4 | >300 |
| CGP70523 | 242 | 16 | 38 |
| Isoguvacine | 1.4[f,k] | inactive at 500[h] | $EC_{50}$ = 99[i] |
| TPMPA | $K_b$ = 320[j] | $EC_{50}$~500[h] | $K_b$ = 2.1[i] |
| PMPA | >100 | >1000[l] | 6.0 |

[a]Receptor affinities are $IC_{50}$ values unless otherwise stated.
[b]$IC_{50}$ values ie. concentration that inhibits 50% of the total [$^3$H]muscimol binding using rat cortical membranes (Froestl et al, 1995a; 1995b).
[c]$IC_{50}$ values for the inhibition of [$^3$H]CGP27492 binding using rat cortical membranes (Froestl et al, 1995a; 1995b).
[d]$IC_{50}$ values for the inhibition of the response of 1 μM GABA using human $r_1$ mRNA expressed in Xenopus oocytes as described in the Materials and Methods section.
[e]$EC_{50}$ values ie. the effective dose that activates 50% of the maximal current when tested at $r_1$ receptors expressed in Xenopus oocytes as described herein.
[f]$IC_{50}$ values for the inhibition of the total Na-independent [$^3$H]GABA binding using rat brain membranes (Johnston et al, 1978).
[g]Data from Kerr and Ong (1995) using guinea pig ileum, in the presence of bicuculline, against baclofen-depression of twitch contractions.
[h]Data from Ragozzino et al (1996) using whole cell patch recordings from pyrimidal neurons in hippocampal slices in the presence of bicuculline (20 μM).
[i]Data from Murata et al (1996) using human $r_1$ mRNA expressed in Xenopus oocytes.
[j]Data from Ragozzino et al (1996) using poly(A)+ RNA from rat cortex expressed in Xenopus oocytes.
[k]$EC_{50}$ values for GABA, CGP27492, CGP35024, TACA, CACA and isoguvacine using poly(A)+ RNA from rat cortex expressed in Xenopus oocytes are 107 μM, 938 μM, inactive at 1 mM, 133 μM, inactive at 5 mM, and 305 μM respectively (Woodward et al, 1993). These values are different to the values obtained from radio-ligand binding assays.
[l]Data from measurement of the frequency of spontaneous discharges in rate neocortical slices using the grease-gap recording system.

EXAMPLE 3

Specificity of $GABA_C$ Antagonists for $GABA_C$ Receptor Subtypes

We have demonstrated that the benchmark $GABA_C$ antagonist, TPMPA, is an order of magnitude less potent at blocking human homo-oligomeric rho-2 receptors than rho-1 $GABA_C$ receptors.

Of particular interest is the dihydro derivative of TPMPA, piperidine-4-(methyl)phosphinic acid (PMPA):

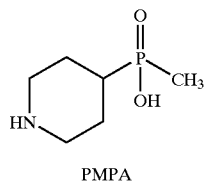

PMPA (Piperid-4-yl)methylphosphinate (PMPA) was synthesized by reduction of a precursor of TMPA and subsequent hydrolysis, as follows:

Platinum oxide ($PtO_2.H_2O$) (50 mg) was added to a solution of recrystallised Troc-precursor (isopropyl [1-(2,2,2-trichloroethoxycarbonyl)-1,2,5,6-tetrahydropyridin-4-yl] methylphosphinate,A) (1.50 g, 3.96 mmol) in methanol (25 mL) and the mixture was shaken with $H_2$ (5 atm.) at room temperature for 24 h. The catalyst was filtered off through Celite, and the residue concentrated under reduced pressure to afford a viscous colourless oil. A n.m.r. examination of the crude reduction product indicated complete reduction of the olefinic bond together with significant concomitant reduction and partial deprotection of the Troc group.

Figure 5:
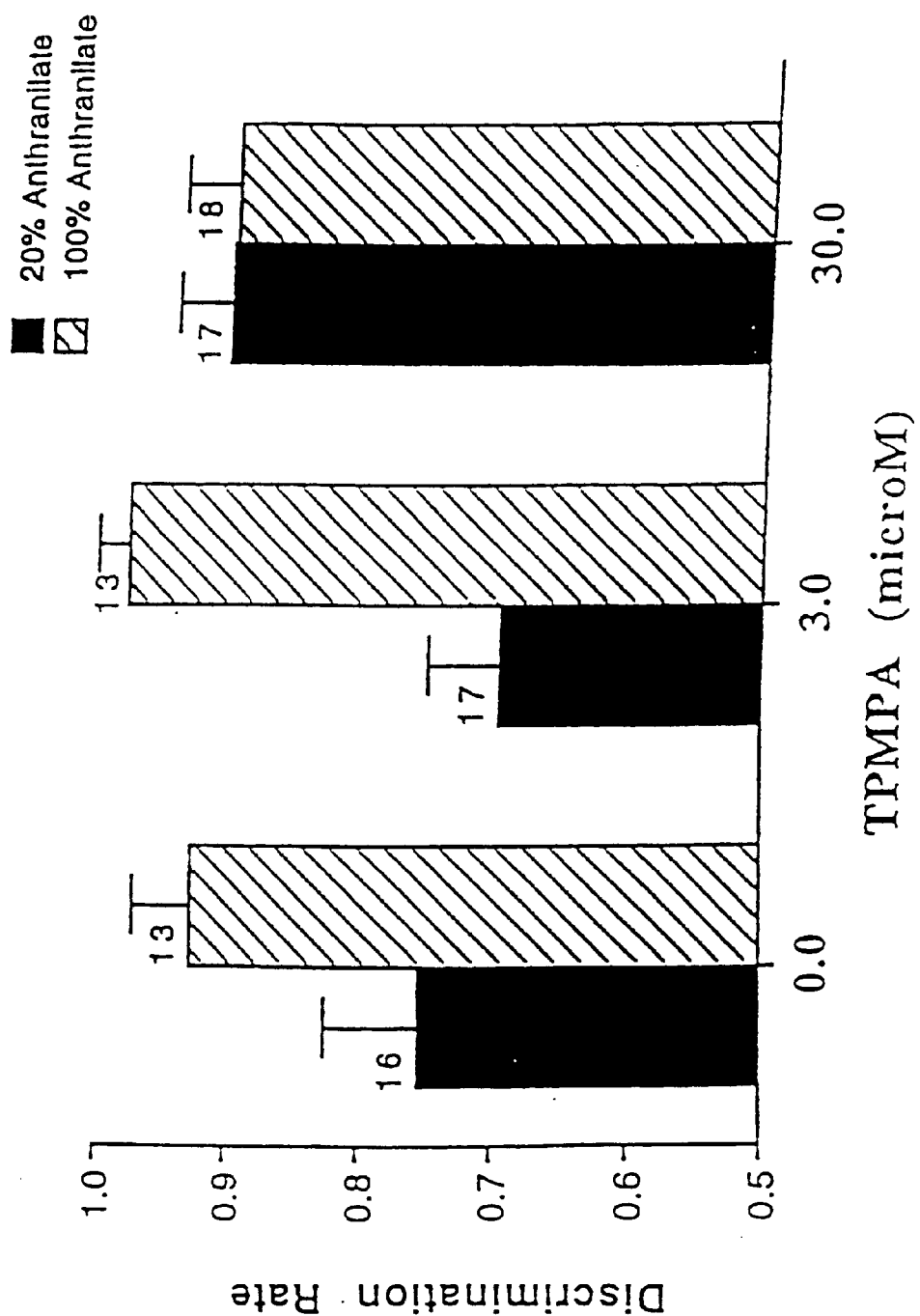
FIG. 5 shows the effect of TPMPA on memory formation in chicks.

A mixture of the residue from above, 48% aq. HBr (40 mL) and glacial acetic acid (40 mL) was refluxed for 60 h. The reaction mixture was concentrated under reduced pressure (water pump) and the final traces of HBr/AcOH were removed by the sequential addition of $H_2O$ and concentration (several cycles). The final residue (HBr salt) was dissolved in a small volume of $H_2O$ and applied to a Dowex AG 50 ($H^+$) column. After initial elution with $H_2O$ until the eluant was neutral, the eluting agent was changed to 1M aq. pyridine. Ninhydrin-positive factions were combined and concentrated under reduced pressure (water pump). Final traces of pyridine were removed by the sequential addition of $H_2O$ and concentration under reduced pressure (several cycles) to afford a quantitative yield of crude (piperid-4-yl) methylphosphinic acid (PMPA)(C) as an off-white solid (ca. 645 mg, air dried) which was recrystallised from $EtOH/H_2O$ (450 mg, 70%): m. p. 289–291°; $_1$H NMR (300 MHz, $D_2O$, Ref: DOH=δ 4.8) δ 1.19 (3H, d, J=13.2 Hz, $PCH_3$), 1.56–1.82 (3H, 2×overlapping m, 2×$NCH_2CH_B$ and PCH), 2.00–2.08 (2H, m, 2×$NCH_2CH_A$), 2.96 (2H, (apparent?) dt, J=3.0, 12.8 Hz, 2×$NCH_BCH_2$), 3.43–3.51 (2H, m, 2×$NCH_ACH_2$); $^{13}C$ NMR ($D_2O$, 75.64 MHz, Ref: (internal) dioxane=δ 67.4) δ 13.6 (d, J=91.5 Hz), 23.1, 36.0 (d, J=96 Hz), 44.8 (d, J=14.2 Hz). The chemical synthesis is shown in FIG. 5.

We have found that PMPA is a much more potent antagonist than TPMPA against rho-2 receptors, and less potent than TPMPA against rho-1 receptors, as indicated in Table 4.

TABLE 4

Binding Affinity for rho-1 and rho-2 Receptors

| $K_B$ (μM) | human rho-1 receptor | human rho-2 receptors |
|---|---|---|
| TPMPA | 2.0 ± 0.4 | 15.6 ± 1.6 |
| PMPA | 6.0 ± 1.2 | 4.2 ± 0.2 |

PMPA and TPMPA show similar weak activity against $GABA_A$ and $GABA_B$ receptors.

The finding that TPMPA and PMPA show differing selectivity between rho-1 and rho-2 subtypes of $GABA_C$ receptors was quite unexpected.

EXAMPLE 4

Effect of TPMPA on Memory

The Effects of TPMPA in Memory Consolidation in Chicks

This procedure trains each chick on anthranilate-coated red beads, which have a bitter taste. In the test, 120 min. after the initial exposure to the red bead each chick is presented with a blue and a red bead, and normally will avoid pecking at the red bead; the discrimination ratio measures how well it remembers to do this. Chicks trained on 100% anthranilate-coated beads produce a discrimination ratio better than 0.9, and drug-induced memory deficits can be detected in this group. However, chicks trained on 20% anthranilate-coated beads produce a discrimination ratio of around 0.6, and this group can be used to detect drug-induced memory enhancement. Drugs are delivered by two bilateral intracranial injections (10 μL each).

Figure 6:
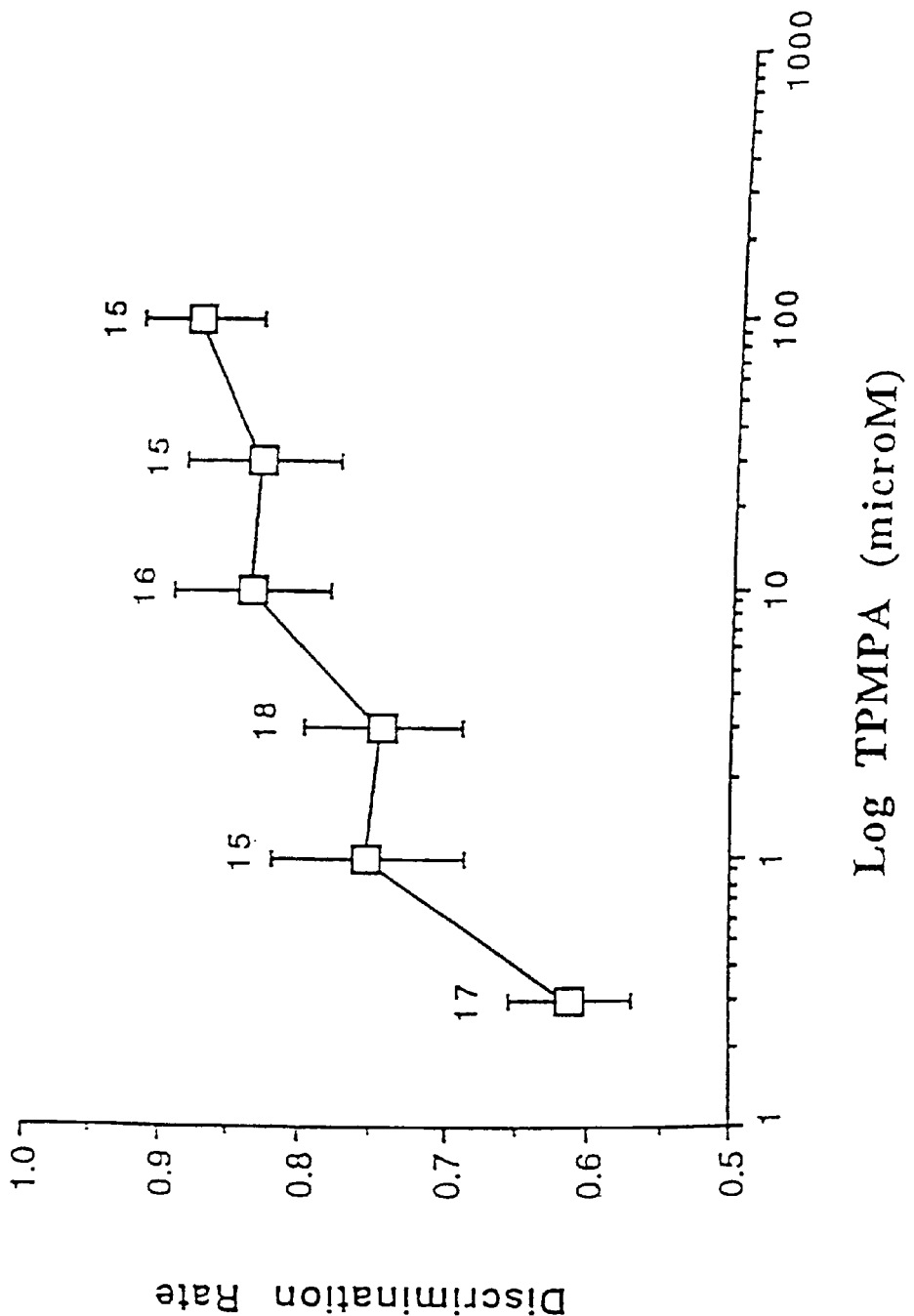
FIG. 6 shows the dose response relationship for the effects of TPMPA on discrimination ratio.
Figure 7:
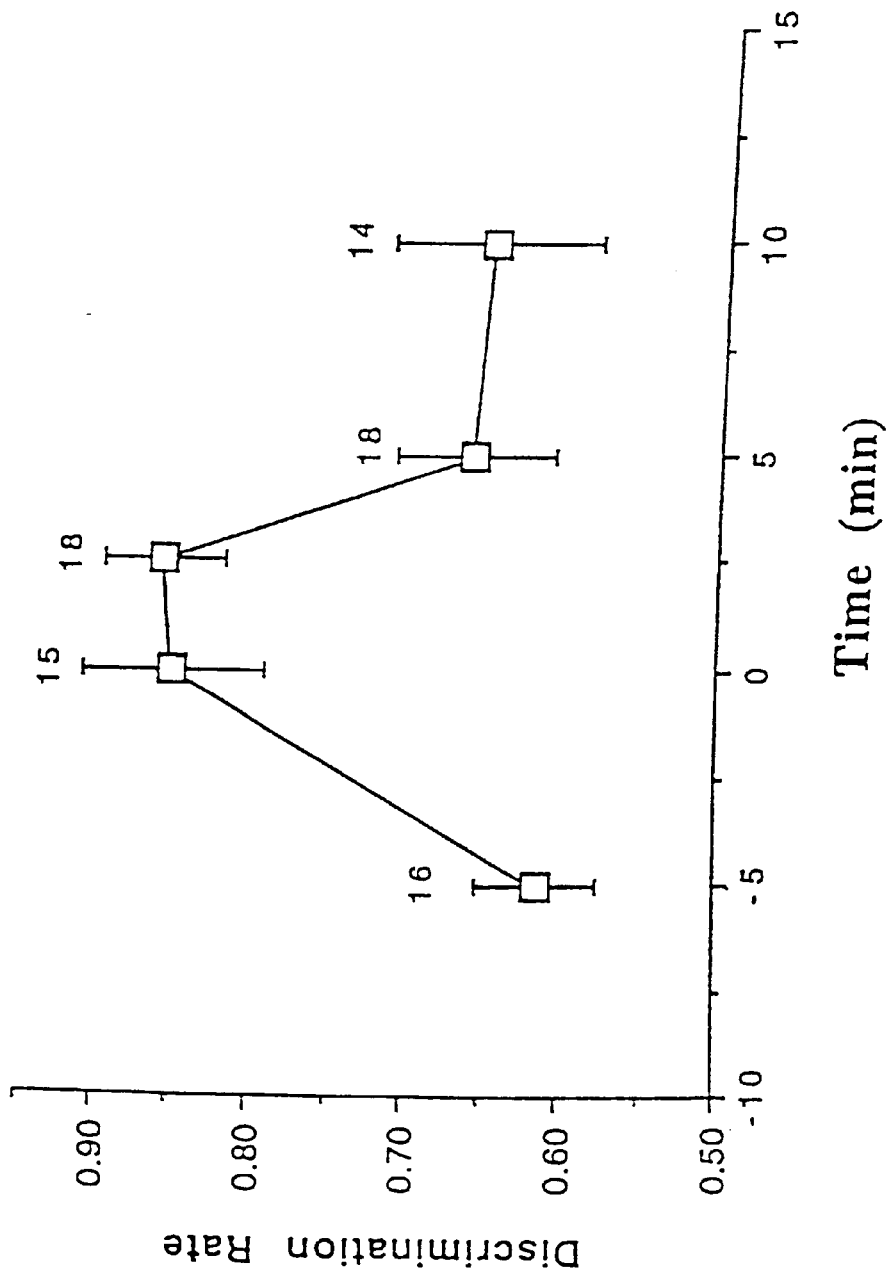
FIG. 7 shows the effect of time after injection of TPMPA on memory formation in chicks.
Figure 8:
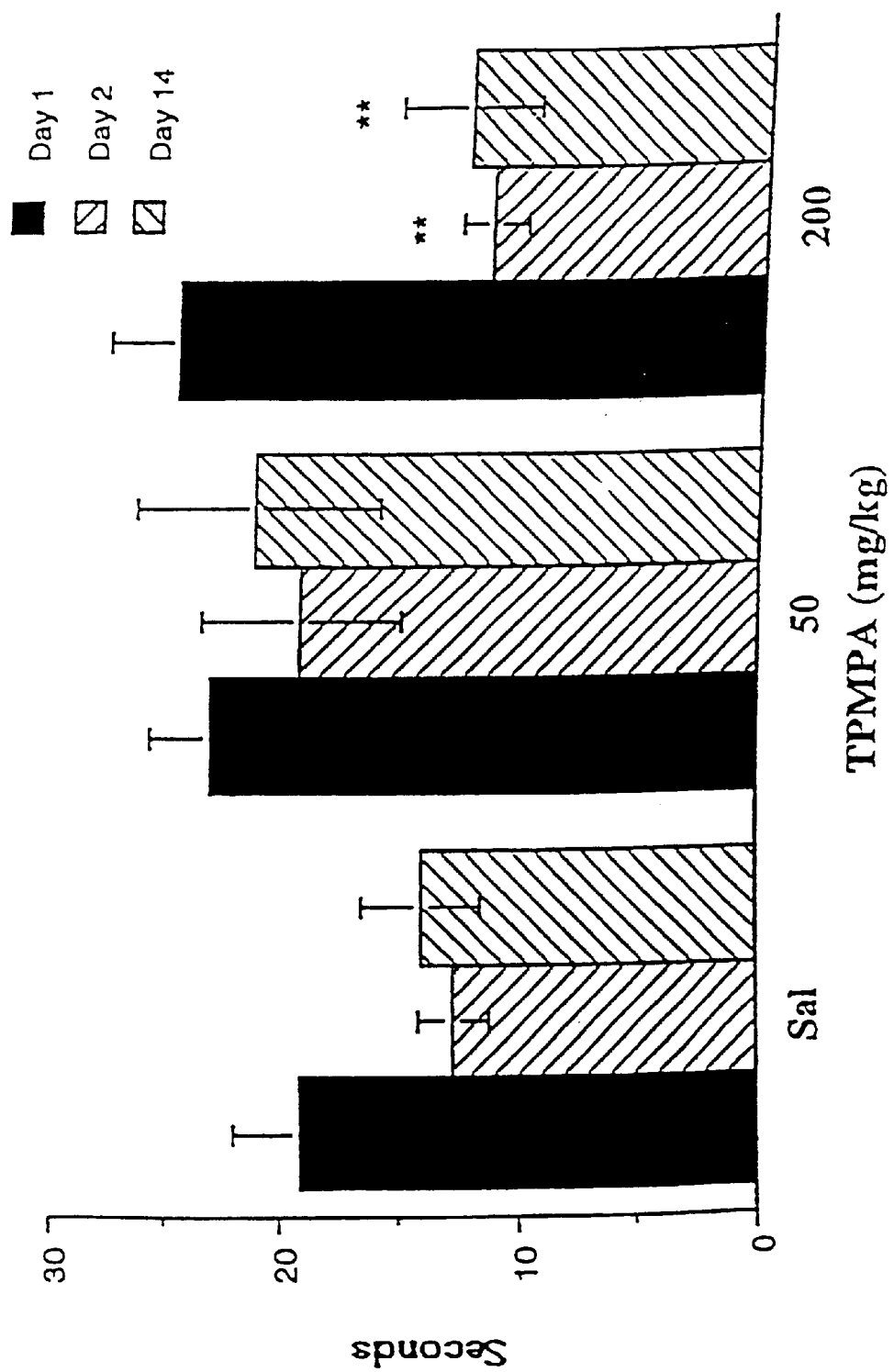
FIG. 8 shows the effect of TPMPA on memory for an elevated plus maze in male Swiss mice.

FIG. 6 shows that TPMPA at a dose of 30 μM enhances memory with the group trained with 20% anthranilate performing as well as the 100% anthranilate group. FIG. 7 shows the dose-response relationship for the effects of TPMPA on discrimination ratio, with an $EC_{50}$ between 1 and 10 μM. FIG. 8 shows the dependence of this effect on time of injection, with an optimum effect produced by injecting in the 2.5 minutes after training.

The Effects of TPMPA on the Plus-maze Memory Test

In this assay mice are trained by placing them at the end of the open arm of the plus maze and allowing them to find the shelter of the closed arms. The time taken is measured as the 'latency'. Immediately after the trial the mice are injected with the test drug or with a saline control. Two and ten days later the test is repeated. An agent which enhances memory consolidation will significantly reduce the latency time relative to the Although the possibility that PMPA might have activity as a competitive antagonist of $GABA_C$ receptors is mentioned in U.S. Pat. No. 5,627,169: "Selective Antagonists for $GABA_{rho}$ Receptor" and in a paper by Woodward et al (1993), it appears that neither this compound nor its analogues was actually synthesised and tested Consequently these prior disclosures are merely speculative paper examples.

CGP36742 was shown to be a moderately potent antagonist at $GABA_B$ receptors using a [$^3H$]-CGP27492 binding assay ($IC_{50}$=35 μM) (Bittiger et al, 1992; Olpe et al, 1993; Froestl et al, 1995a). It had weak effects at $GABA_A$ receptors ($IC_{50}$=500 μM) (Bittiger et al, 1992), and had no effect at other receptor types, including NMDA, benzodiazepine, quisqualate, kainate, muscarinic cholinergic, adrenergic, serotoninergic and histaminergic receptors (1 mM) (Bittiger et al, 1992; Froestl et al, 1995b). However, we have now found that CGP36742 showed moderate antagonist activity at $GABA_C$ receptors ($IC_{50}$ =62 μM), and that its apparent selectivity for $GABA_B$ compared to $GABA_C$ receptors was approximately 2-fold. This compound has shown promising therapeutic potential in the treatment of cognitive deficits, petit mal epilepsy and depression (Bittiger et al, 1992). Therefore it is possible that antagonism of $GABA_C$ receptors contributes to the cognitive enhancement potentiation by CGP36742, such enhancement is not shown by other orally-active $GABA_B$ receptor antagonists (Froestl et al, 1995b).

TPMPA was recently synthesised and tested at $GABA_A$, $GABA_B$, and $GABA_C$ receptors (Murata et al, 1996). It is a conformationally-restricted analogue of CGP44530, and is the methylphosphinic analogue of isoguvacine. It was found to be more than 100-fold more selective as an antagonist for $GABA_C$ receptors than for $GABA_B$ receptors, and is 500-fold more selective at $GABA_C$ receptors than at $GABA_A$ receptors (Murata et al, 1996; Ragozzino et al, 1996). saline controls. The results are summarized in FIG. 9, and show that TPMPA at 200 mg/Kg, but not at 50 mg/Kg, significantly reduces the latency in the 14 day test. This is consistent with enhancement of memory consolidation. When we repeated the experiment, this time testing only after 14 days and using Swiss mice from a different source, we found that TPMPA at 50 mg/Kg but not 200 mg/Kg significantly reduced latency. The experiments overall are therefore positive but inconclusive, since the different origin of the mice may be a contributing factor.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Arunlakshana, O. and Schild, H. O. Br. J. Pharmacol., 1959 14 48–58

Bittiger, H., Bernasconi, R., Froestl, W., Hall, R., Jaekel, J., Klebs, K., Krueger, L., Mickel, S. J., Mondadori, C., Olpe, H. R., Pfannkuch, F., Pozza, M., Probst, A., Van Riezen, H., Schmutz, M., Schuetz, H., Steinmann, M. W., Vassout, A., Waldmeier, P. Pharmacol. Com., 1992 2 70–74

Bittiger, H., Froestl, R. W., Mickel, S. J., Olpe, H. R., 1993 Trends Pharmacol. Sci., 1993 14 391–393

Bormann, J. and Feigenspan, A. Trends Neurosci., 1995 18 515–519

Cutting, G. R., Lu, L., O'Hara, B., Kasch, L. M., Donovan, D., Shimada, S., Antonarakis, S. E., Guggino, W. B., Uhl, G. R. and Kazazian H. H. Proc. Natl. Acad. Sci. USA., 1991 88 2673–2677

Cutting, G. R., Curristin, S., Zoghbi, H., O'Hara, B., Seldin, M. F. and Uhl G. R. Genomics, 1992 12 801–806

Dong, C-J., Picaud, S. A. and Weblin, F. S. J. Neurosci., 1994 14 2648–2658

Enz, R., Brandstatter, J. H., Hartveit, E., Wassle, H. and Bormann, J. Eur. J. Neurosci., 1995 7 1495–1501

Froestl, W., Mickel, S. J., von Sprecher, G., Bittiger, H. and Olpe H-R. Pharmacol. Com., 1992 2 52–56

Froestl, W., Mickel, S. J., Hall, R. G., von Sprecher, G., Strub, D., Baumann, P. A., Brugger, F., Gentsch, C., Jaekel, J., Olpe, H-R., Rihs, G., Vassout, A., Waldmeier, P. C. and Bittiger H. J. Med. Chem., 1995a 38 3297–3312

Froestl, W., Mickel, S. J., von Sprecher, G., Diel, P. J., Hall, R. G., Maier, L., Strub, D., Melillo, V., Baumann, P. A., Bernasconi, R., Gentsch, C., Hauser, K., Jaekel, J., Karlsson, G., Klebs, K., Maitre, L., Marescaux, C., Pozza, M. F., Schmutz, M., Steinmann, M. W., van Riezen, H., Vassout, A., Monadori, C., Olpe, H-R., Waldmeier, P. C. and Bittiger H. J. Med. Chem., 1995b 38 3313–3331

Johnston, G. A. R., Curtis, D. R., Beart, P. M., Game, C. J. A., McCulloch, R. M. and Twitchin, B. J. Neurochem., 1975 24 157–160

Johnston, G. A. R., Allan, R. D., Kennedy, S. M. E. and Twitchin, B. 1978 "GABA-Neurotransmitters", Alfred Benzon Symposium 12, Munksgaard, p 149–164.

Johnston, G. A. R. Pharmacol. Ther., 1996a 69 173–198

Johnston, G. A. R. Trends Pharmacol. Sci., 1996b 17 319–323

Kerr, D. I. B. and Ong, J. Pharmacol. Ther., 1995 67 187–246

Kusama, T., Spivak, C. E., Whiting, P., Dawson, V. L., Schaeffer, J. C. and Uhl G. R. Br. J. Pharmacol., 1993a 109 200–206

Kusama, T., Wang, T-L., Guggino, W. B., Cutting, G. R., Uhl, G. R. 1993b Eur. J. Pharmacol.-Mol. Pharmacol. Sect., 1993b 245 83–84

Lukasiewicz, P. D., Maple, B. R. and Weblin, F. S. J. Neurosci., 1994 14 1202–1212

Murata, Y., Woodward, R. M., Miledi, R. and Overman, L. E. Bioorg. and Med. Chem. Lett., 1996 6 2071–2076

Olpe; H-R., Karlsson, G., Pozza, M. F., Brugger, F., Steinmann, M. W., Van Riezen, H., Fagg, G., Hall, R. G., Froestl, W. and Bittiger, H. Eur. J. Pharmacol., 1990 187 27–38

Olpe, H-R., Steinmann, M. W., Ferrat, T., Pozza, M. F., Greiner, K., Brugger, F., Froestl, W., Mickel, S. J. and Bittiger, H. Eur. J. Pharmacol., 1993 233 179–186

Ogurusu, T. and Shingai, R. Biochimica et Biophysica Acta., 1996 1305 15–18

Polenzani, L., Woodward, R. M., Miledi, R. Proc. Natl. Acad. Sci. USA, 1991 88 4318–4322

Qian, H. and Dowling, J. E. Nature, 1993 361 162–164

Ragozzino, D., Woodward, R. M., Murata, F., Eusebi, F., Overman, L. E. and Miledi, R. Mol. Pharmacol., 1996 50 1024–1030

Shimada, S., Cutting, G. and Uhl, G. R. Mol. Pharmacol., 1992 41 683–687

Wang, T-L., Guggino, W. B. and Cutting, G. R. J. Neurosci., 1994 14 6524–6531

Woodward, R. M., Polenzani, L. and Miledi, R. Mol. Pharmacol., 1993 43 609–625

What is claimed is:

1. A method of enhancing cognitive activity in an animal, comprising administering to an animal in need of such treatment an effective amount of a compound that has $GABA_C$ receptor antagonist activity and selectivity for the rho-2 subtype of $GABA_C$ receptors, the compound having formula I or formula II:

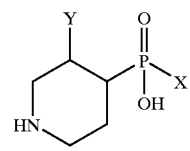

(I)

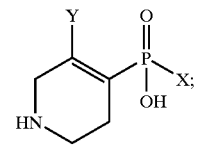

(II)

wherein X represents hydrogen, an alkyl group, an alkyl group substituted with a halogen, or a hydroxyalkyl group, and Y represents hydrogen, a halogen, an alkyl, alkenyl, alkynyl, alkoxy or acyl group, or an alkyl, alkenyl, alkynyl, alkoxy or acyl group that is substituted with halogen, nitrile, or $NO_2$.

2. A method according to claim 1, wherein the compound has selective antagonist activity against $GABA_C$ receptors compared to $GABA_B$ receptors.

3. A method according to claim 1, wherein the compound has selective antagonist activity against $GABA_C$ receptors compared to $GABA_A$ receptors.

4. A method according to claim 1, wherein the compound is substantially inactive against both $GABA_A$ and $GABA_B$ receptors.

5. A method according to claim 1, wherein the compound comprises a phosphinic acid group.

6. A method according to claim 5, wherein the compound comprises a phosphinic acid group that is substituted with an alkyl group of 1 to 6 carbon atoms.

7. A method according to claim 1, wherein the compound comprises a double bond that imposes a conformational restriction or rotation about the bond corresponding to the C3–C4 bond of GABA.

8. A method according to claim 7, wherein the compound is a conformationally-restricted analogue of CGP44530 in which rotation about the C3–C4 bond is restricted.

9. A method according to claim 1, wherein X is methyl or ethyl.

10. A method according to claim 1, wherein the compound comprises a halogen selected from the group consisting of chlorine and fluorine.

11. A method according to claim 1, wherein the compound is PMPA.

12. A method according to claim 1, wherein enhancing cognitive activity in the animal comprises stimulating memory capacity in the animal.

13. A method according to claim 1, wherein the animal is suffering from a condition selected from the group consisting of cognitive deficit, memory impairment, and dementia.

14. A method according to claim 1, wherein the animal is suffering from dementia, Alzheimer's disease, AIDS, or schizophrenia.

15. A method according to claim 1, wherein the animal is a human.

16. A method according to claim 1, wherein the compound is administered orally.

* * * * *